United States Patent
Ghani et al.

(10) Patent No.: US 11,707,425 B2
(45) Date of Patent: Jul. 25, 2023

(54) HAIR TREATMENT COMPOSITIONS CONTAINING PECTIN AND CATIONIC COMPOUNDS

(71) Applicant: L'OREAL, Paris (FR)

(72) Inventors: Sana Ghani, Elizabeth, NJ (US); Aziza Khader Suleiman, Paterson, NJ (US); Vanessa Comeron-Decarlo, Roselle Park, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/555,309

(22) Filed: Aug. 29, 2019

(65) Prior Publication Data

US 2021/0059922 A1    Mar. 4, 2021

(51) Int. Cl.
| | | |
|---|---|---|
| *A61Q 5/06* | (2006.01) | |
| *A61Q 5/12* | (2006.01) | |
| *A61K 8/73* | (2006.01) | |
| *A61K 8/34* | (2006.01) | |

(52) U.S. Cl.
CPC .............. *A61K 8/731* (2013.01); *A61K 8/342* (2013.01); *A61K 8/732* (2013.01); *A61Q 5/06* (2013.01); *A61Q 5/12* (2013.01)

(58) Field of Classification Search
None
See application file for complete search history.

(56) References Cited

U.S. PATENT DOCUMENTS

| | | | | |
|---|---|---|---|---|
| 5,002,761 | A * | 3/1991 | Mueller | A61K 8/24 424/70.1 |
| 2004/0106529 | A1 | 6/2004 | Fack et al. | |
| 2004/0115155 | A1* | 6/2004 | Salvador | A61K 8/39 424/70.13 |
| 2006/0193817 | A1* | 8/2006 | Uehara | A61Q 19/00 424/70.122 |
| 2013/0272970 | A1 | 10/2013 | Pimenta et al. | |
| 2019/0029948 | A1 | 1/2019 | Akerele et al. | |
| 2019/0125650 | A1* | 5/2019 | Lee | A61Q 5/02 |

FOREIGN PATENT DOCUMENTS

| | | | | |
|---|---|---|---|---|
| EP | 2095845 A2 * | 9/2009 | | A61Q 5/004 |
| WO | 2019/094892 A1 | 5/2019 | | |

OTHER PUBLICATIONS

International Search Report and Written Opinion dated Dec. 21, 2020 for corresponding PCT Application No. PCT/US2020/053010.

* cited by examiner

*Primary Examiner* — Jyothsna A Venkat
(74) *Attorney, Agent, or Firm* — Polsinelli PC (57) ABSTRACT

The instant disclosure relates to hair treatment compositions that include a unique combination of components that function to impart desirable cosmetic properties to the hair. The hair treatment compositions typically include a cationic cellulosic quaternary ammonium compound; pectin; a cationic surfactant including cationizable surfactants together with an acid neutralizer; glyceryl ester; fatty alcohol; polyol; and water; wherein the weight ratio of the cationic cellulosic quaternary ammonium compound to pectin is from about 0.5 to about 5.

3 Claims, 2 Drawing Sheets

Invention Formula A
Left side

Slipper coating
Even distribution
Absorption
Clean hands
Supple

Commercial Product E
Right side

Waxy coating

——————— DECONSTRUCT ———————

Visual fast drying
Global Volume
Curl regularity
Curl evenness

Open ends
Irregular
Weighed down

HAIR TREATMENT COMPOSITIONS CONTAINING PECTIN AND CATIONIC COMPOUNDS

FIELD OF THE DISCLOSURE

The instant disclosure relates to hair treatment compositions that are particularly useful for improving the quality of hair and which can impart beneficial properties such as styling/shaping, frizz control, retention of shape/curl, curl pick up, discipline as well as hydration, moisture, and smoothness. Also disclosed are methods for using the hair treatment compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades, which m requires the use of oxidizing agents.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, different types of hair styling products have been developed by manufacturers that are aimed to help consumers achieve a desired look, including one or more of fuller hair, thicker hair, sleek and straight hair, frizz-free hair, and defined curls. These products are typically provided in forms that are applied after the shampooing and conditioning processes are completed.

In one example, styling products are available that provide protection against external factors such as protection from moisture to minimize or reduce frizziness. To achieve this benefit, a water-resistant film or coating may be applied to the hair using film-forming polymers. Depending on the chemical make-up of the film-forming polymers. Product formulations that include these polymers can tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

Increasingly, consumers also seek hair products that have a natural look and feel, impart good styling benefits to hair, are durable, and lack the drawbacks of current products, such as the stiff and crunchy effects created by the thick coatings of many styling products. Further, consumers seek products that offer multiple benefits, for example, combining frizz reduction and style hold with softening, straightening and curl definition. Moreover, consumers desire hair products that can protect hair from extreme environmental conditions such as high humidity which causes the hair to become very frizzy, unmanageable, and lose its shape and style.

One important functional element of such products is their ability to style the hair without weighing it down. Many consumers seek hair products which have excellent style memory, cosmeticity, and shine without heavily coating the hair strands, and thereby weighing the hair down and often times exhibiting a brittle or crunchy film. The resulting feel and texture of the hair after the application are important elements of such commodities. While different technologies and products exist in the market for hair styling products, there is still a need for improvement in these areas as well as the need to provide caring benefits that are not typically found in a styling product.

Thus, the object of this invention is related to a composition and method of treating hair utilizing hair compositions which will impart both caring and styling/shaping benefits such as frizz control, and promote curl definition, curl/shape retention, curl pick up, discipline, control/hold, softness, smoothness, shine, natural feel, and hydration, but will not result in any product build up or leave the hair feeling heavily coated or weighed down, crunchy, stiff, or brittle. The object of the invention is also to provide these attributes that will last even when hair is exposed to high humidity conditions. The invention is particularly useful for treating and providing the described properties to curly hair (of varying degrees of curl) and to wavy hair.

SUMMARY OF THE DISCLOSURE

It has surprisingly been found that compositions and methods of treating hair according to the present invention impart styling/shaping, curl definition, curl retention, curl pick up, frizz control, control/hold, discipline, hydration, moisture, and smoothness and other cosmetic benefits to the hair.

One aspect of the invention pertains to a hair treatment composition comprising:
(a) at least one cationic cellulosic quaternary ammonium compound;
(b) pectin, in an amount of about 0.01 to about 10 wt. %, based on the total weight of the hair treatment composition;
(c) at least one cationic surfactant;
(d) at least one glyceryl ester;
(e) at least one fatty alcohol;
(f) at least one polyol; and
(g) water;
wherein the weight ratio of the cationic cellulosic quaternary ammonium compound to pectin is from about 0.5 to about 5 or about 0.75 to about 4, or about 1 to about 3, or about 1 to about 2, or is at about 1.5, 1.25, or 1.0.

Another aspect of the invention pertains to methods of treating hair. In some embodiments, the method comprises applying any of the compositions described herein to hair. In one or more embodiments, the composition is applied to hair as part of a hair styling/shaping or caring routine. In some embodiments, the composition is applied after treating the hair with a shampoo and/or conditioner.

BRIEF DESCRIPTION OF THE DRAWING

Implementation of the present technology will now be described, by way of example only, with reference to the attached figures, wherein.

It should be understood that the various aspects are not limited to the arrangements and instrumentality shown in the drawings.

DETAILED DESCRIPTION OF THE DISCLOSURE

The term "hair treatment composition" encompasses many types of compositions for application to the hair, for example, hair lotions, hair creams, hair gel creams, hair conditioners, hair masques (masks), etc., which can be used either as leave-on or rinse-off treatments or products. A hair treatment composition according to the invention is characterized by its ability to provide a cosmetic (such as styling/shaping and caring) benefit to the hair. Non-limiting examples of benefits that can be imparted by the compositions of the present invention to hair include frizz control, curl definition, curl retention, curl pick-up, styling/shaping, discipline, frizz control, hold/control, manageability, smoothness, softness, suppleness, hydration (does not feel dry) and natural feel.

The hair treatment compositions of the instant disclosure typically include:
 (a) at least one cationic cellulosic quaternary ammonium compound;
 (b) pectin, in an amount of about 0.01 to about 10 wt. %, based on the total weight of the hair treatment composition;
 (c) at least one cationic surfactant, including cationizable surfactants together with an acid neutralizer;
 (d) at least one glyceryl ester;
 (e) at least one fatty alcohol;
 (f) at least one polyol; and
 (g) water;
wherein the weight ratio of the cationic cellulosic quaternary ammonium compound to pectin is from about 0.5 to about 5 or about 0.75 to about 4, or about 1 to about 3, or about 1 to about 2, or is at about 1.5, 1.25, or 1.0.

In one embodiment, the at least one cationic cellulosic quaternary ammonium compound is selected from a copolymer of hydroxyethyl cellulose and of diallyldimethylammonium chloride (Polyquaternium-4), salts of hydroxyethyl cellulose reacted with trimethyl ammonium substituted epoxide (Polyquaternium 10), salts of hydroxyethyl cellulose reacted with a trimethyl ammonium substituted epoxide and a lauryl dimethyl ammonium substituted epoxide (polyquaternium-67), or mixtures thereof.

In an embodiment, the at least one cationic cellulosic quaternary ammonium compound is polyquaternium-4.

In an embodiment, the at least one cationic cellulosic quaternary ammonium compound is polyquaternium-10.

In an embodiment, the at least one cationic cellulosic quaternary ammonium compound is polyquaternium-67.

In an embodiment, the at least one cationic cellulosic quaternary ammonium compound comprises polyquaternium-4 and a second cationic cellulosic quaternary ammonium compound.

In an embodiment, the at least one cationic surfactant is selected from:
 quaternary ammonium salts corresponding to the general formula below:

in which the groups R8 to R11 which may be identical or different, represent a linear or branched, saturated or unsaturated aliphatic group comprising from 1 to 30 carbon atoms, or an aromatic group such as aryl or alkylaryl, at least one of the groups R8 to R11 denoting a group comprising from 8 to 30 carbon atoms;
 a quaternary ammonium salt of imidazoline;
 a quaternary diammonium or triammonium salt, in particular of formula:

in which R16 denotes an alkyl radical comprising approximately from 16 to 30 carbon atoms, which is optionally hydroxylated and/or interrupted with one or more oxygen atoms, R17 is chosen from hydrogen or an alkyl radical comprising from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates;
 cationizable surfactants, including cationizable surfactants together with an acid neutralizer, for example of the general structure $R_4$-A-$R_5$-B
 wherein R4 is a saturated or unsaturated, straight or branched alkyl chain with 8 to 24 C atoms, R5 is a straight or branched alkyl chain with 1 to 4 C atoms, A is selected from:

and B is selected from wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms, or mixtures thereof.

In an embodiment, the at least one cationic surfactant comprises at least one cationizable surfactant. In some embodiments, the cationizable surfactant is neutralized with an acid neutralizer such as an organic acid, for example, tartaric acid or lactic acid.

In an embodiment, the at least one glyceryl ester is selected from:
- esters of an oligomeric glycerol, especially the esters of diglycerol, in particular the condensates of adipic acid and of glycerol, for which a portion of the hydroxyl groups of the glycerols have reacted with a mixture of fatty acids, such as steric acid, capric acid, stearic and isostearic acid and 12-hydroxystearic acid, such as, in particular, those sold under the trade mark SOFTISAN 649 by the company Cremer Oleo or under the trademark SP SUPERMOL B MBAL-SS-(RB) by the company Croda, such as bis-diglyceryl polyacyladipate-2,
- the arachidyl propionate sold under the trade mark WAXENOL 801 by Alzo,
- phytosterol esters, triglycerides of fatty acids and derivatives thereof, such as hydrogenated cocoglycerides,
- noncrosslinked polyesters resulting from the poly condensation between a linear or branched C4-C50 dicarboxylic acid or polycarboxylic acid and a C2-C50 diol or polyol,
- aliphatic esters of an ester resulting from the esterification of an aliphatic hydroxycarboxylic acid ester with an aliphatic carboxylic acid,
- or mixtures thereof.

In an embodiment, the at least one glyceryl ester is selected from bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, or a mixture thereof.

In an embodiment, the at least one glyceryl ester includes bis-diglyceryl polyacyladipate-2.

In an embodiment, the at least one glyceryl ester includes glyceryl behenate, glyceryl caprate, glyceryl cocoate, glyceryl oleate, glyceryl stearate, glyceryl dioleate, glyceryl distearate, glyceryl laurate, or mixtures thereof. In an embodiment, the at least one glyceryl ester includes bis-diglyceryl polyacyladipate-2 and a second glyceryl ester selected from glyceryl behenate, glyceryl caprate, glyceryl cocoate, glyceryl oleate, glyceryl stearate, glyceryl dioleate, glyceryl distearate, and glyceryl laurate.

In an embodiment, the at least one fatty alcohol is selected from cetyl alcohol, stearyl alcohol, cetearyl alcohol, behenyl alcohol, myristyl alcohol, or mixtures thereof.

In an embodiment, the at least one polyol is selected from hexylene glycol, butylene glycol, propylene glycol, dipropylene glycol, caprylyl glycol, glycerin, or mixtures thereof.

In an embodiment, the at least one polyol is selected butylene glycol, propylene glycol, glycerin, or mixtures thereof.

In an embodiment, the compositions of the present invention is substantially free or is free of silicones, In an embodiment, the compositions of the present invention is substantially free or is free of non-ester oils.

In various embodiments, the weight ratio of the cationic cellulosic quaternary ammonium compound to pectin is from about 0.5 to about 5 or about 0.75 to about 4, or about 1 to about 3, or about 1 to about 2, or is at about 1.5, 1.25, or 1.0, including ranges and sub-ranges there between.

In various embodiments, the weight ratio of the cationic cellulosic quaternary ammonium compound to pectin is at about 0.5, about 0.75, about 1, about 1.1, about 1.2, about 1.25, about 1.3, about 1.35, about 1.4, about, 1.45, about 1.5, about 1.6, about 1.7, about 1.8, about 1.9, or about 2.

The present invention also relates to a method of treating hair, the method comprising applying any one of the above-described compositions of the invention to hair. Said method comprises providing to hair one or more of:
- shaping or styling benefits;
- curl definition;
- curl retention;
- long-lasting curl definition;
- humidity-resistant curl definition;
- frizz control;
- smoothness;
- softness;
- natural feel;
- hydration;
- light-weight feel;
- manageability; or
- shine and luster.

The above compositions, which feature a unique combinations of ingredients, advantageously provide frizz control, curl definition, curl retention, curl pick-up, discipline, hold/control, styling/shaping, long lasting or humidity-resistant styling and curl care benefits together with natural feel, light-weight feel, softness, and smoothness.

The hair treatment compositions described herein may be in any suitable physical form. Suitable forms include, but are not limited to low to moderate viscosity liquids, lotions, milks, gel creams, creams, pastes, clays, conditioners, masks, and the like.

The hair treatment compositions may be packaged in a variety of different containers, such as, for example, a ready-to-use container. Non-limiting examples of useful packaging include tubes, jars, caps, unit dose packages, and bottles, including squeezable tubes and bottles and spray bottles.

Cationic Cellulosic Quaternary Ammonium Compound

Non-limiting examples of cationic cellulosic quaternary ammonium compounds include cationic polymers such as a copolymer of hydroxyethyl cellulose and of diallyldimethylammonium chloride (Polyquaternium-4), salts of hydroxyethyl cellulose reacted with trimethyl ammonium substituted epoxide (Polyquaternium 10), salts of hydroxyethyl cellulose reacted with a trimethyl ammonium substituted epoxide and a lauryl dimethyl ammonium substituted epoxide (polyquaternium-67), and a mixture thereof.

The total amount of the at least one cationic cellulosic quaternary ammonium compound may vary, but in some cases, the total amount is about 0.05 to about 5 wt. %, based on the total weight of the hair treatment composition. In some cases, the total amount of the at least one cationic cellulosic quaternary ammonium compound is about 0.1 to about 4 wt. %, about 0.15 to about 3 wt. %, about 0.2 to about 2 wt. %, based on the total weight of the hair treatment composition, including ranges and sub-ranges there between.

In some embodiments, the total amount of the at least one cationic cellulosic quaternary ammonium compound is at about 0.05, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1 wt. %, based on the total weight of the hair treatment composition.

Pectin

The total amount of pectin may vary, but in some cases, the total amount is about 0.01 to about 10 wt. %, based on the total weight of the hair treatment composition. In some cases, the total amount of pectin is about 0.05 to about 10 wt. %, about 0.05 to about 8 wt. %, about 0.05 to about 6 wt. %, about 0.05 to about 5 wt. %, about 0.1 to about 4 wt. %, about 0.15 to about 4 wt. %, about 0.15 to about 3 wt. %, about 0.2 to about 3 wt. %, about 0.2 to about 2 wt. %, based on the total weight of the hair treatment composition, including ranges and sub-ranges there between.

In some embodiments, the total amount of pectin is at about 0.01, 0.015, 0.02, 0.025, 0.03, 0.035, 0.04, 0.045, 0.05, 0.06, 0.07, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1 wt. %, based on the total weight of the hair treatment composition, including ranges and sub-ranges there between.

Cationic Surfactants Including Cationizable Surfactants

In accordance with the disclosure, compositions hereof may include at least one cationic surfactant. The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenam idopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearam idopropyldimethylamine, behenam idopropyldimethylamine, behenam idopropyldiethylamine, behenam idoethyldiethyl-amine, behenam idoethyldimethylamine, arachidam idopropyldimethylamine, arachidam idopropyidiethylamine, arachidam idoethyidiethylamine, arachidam idoethyidimethylamine, brassicam idopropyldimethylamine, lauram idopropyl dimethylamine, myristam idopropyl dimethylamine, dilinoleam idopropyl dimethylamine, palmitamidopropyl dimethylamine, and mixtures thereof.

In some embodiments, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenam idoethyldimethylamine, arachidam idopropyldimethylamine, arachidam ido-propyidiethylamine, arachidam idoethyidiethylamine, arachidam idoethyidimethylamine, and mixtures thereof.

In some embodiments, the cationic surfactant comprises cetrimonium chloride, behentrimonium chloride, and mixtures thereof. Behentrimonium Chloride, also described by the technical names that include 1-Docosanaminium, N,N,N-Trimethyl-, Chloride, and N,N,N-Trimethyl-1-Docosanaminium Chloride, is the quaternary ammonium salt that conforms to the formula:

(I)

In accordance with some embodiments, the amount of each of the at least one cationic surfactant is from about 0.1 to about 10 wt. %, or from about 0.5 to about 8 wt. %, or from about 1 to about 6 wt. %, or from about 1.5 to about 5 wt. % or any suitable combination, sub-combination, range, or sub-range thereof by weight, based on the weight of the composition. One of ordinary skill in the art, however, will appreciate that other ranges are within the scope of the invention. In some particular embodiments, the at least one cationic surfactant, including cationizable surfactants together with an acid neutralizer, is present from about 0.5 to about 5 wt. %, and in some particular embodiments is present from about 1 to about 3 wt. %, and when present, an acid neutralizer is present from about 0.1 to about 0.5 wt. %, based on the weight of the composition.

Thus, any one of the at least one cationic surfactant is present, by weight, based on the total weight of the composition, from about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.4, 2.5, 2.6, 2.7, 2.8, 2.9, 3, 3.2, 3.4, 3.5, 3.6, 3.8, 4, 4.2, 4.4, 4.5, 4.6, 4.8, 5, 6, 7, 8, 9, to about 10 wt. %, including increments and ranges therein and there between.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cet- rimonium chloride, cethylamine hydrofluoride, chlorallyl-methenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylamino-ethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include: those corresponding to the general formula below:

in which the groups $R_8$ to $R_{11}$ which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and, in some embodiments, from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palm itylam idopropyltrimethylammonium salts, stearamidopropyltrimethylammonium salts and stearamidopropyldimethylcetearylammonium salts.

B. a quaternary ammonium salt of imidazoline, such as, for example, those of formula below:

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups , in some embodiments, comprise, respectively, from 1 to 20 carbon atoms and from 6 to 30 carbon atoms. $R_{12}$ and $R_{13}$ in some embodiments, denote a mixture of alkenyl or alkyl groups containing from 12 to 21 carbon atoms, derived for example from tallow fatty acids, $R_{14}$ in some embodiments, denotes a methyl group, and $R_{15}$, in some embodiments, denotes a hydrogen atom. Such a product is sold, for example, under the name REWOQUAT W 75 by the company Rewo;

C. a quaternary diammonium or triammonium salt, in particular of formula:

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75),

D. Cationic/cationizable surfactants, including cationizable surfactants together with an acid neutralizer, for example of the general structure R4-A-R5-B wherein R4 is a saturated or unsaturated, straight or branched alkyl chain with 8 to 24 C atoms, R5 is a straight or branched alkyl chain with 1 to 4 C atoms, A is selected from:

and B is selected from wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, in some embodiments, 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearam idopropyl amine, stearamidopropyl dimethylamine, steara midopropyl diethylamine, stearamidopropyldibutylamine, stearamidopropylbutylamine, stearamidopropyl dipropylamine, behenamidopropyl propylamine, behenamidopropyl dihydroxyethylamine, behenam idopropyl hydroxyethylamine, behenam idopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenam idopropyl propylamine, behenam idopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl, hydroxyethylamine, dipalmitamidopropyl hydroxyproplamine, dilauramidopropyl amine, dilauramidopropyl methylamine, dilauramidopropyl buylamine, dilauramidopropyl hydroxyethylamin, dilauramidopropyl hydroxyproplamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethylammonium chloride, distearylamidopropyl dimethyl ammonium chloride, dicetylaidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, hydroxyethylamine, palmitoylpropyl dihydrooxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroexyethylamine, myristoylpropyl hydroexyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethlamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropl dipropylamine, behenylpropyl propylamine, behenylpropyl dihydroxyethylamine, behenylpropyl hydroxyethylamine, behenylpropyl dihydroxyethylamine, behenylpropyl hydroxyethylamine, dipalmitoylpropyl methylamine, dipalmitoylpropyl ethylamine, dipalmitoylpropyl butylamine, dipalmitylpropyl propylamine, dipalmitylpropyl hydroxyethylamine, dipalmitylpropyl hydroxypropylamine, dilauroylpropyl amine, dilauroypropyl methylamine, dilauroypropyl methylamine, dilauroylpropyl buylamine, dilauroylpropyl hydroxyethylamine, dilauroylpropyl hydroxypropylamine, distearylpropyl amine, distearylpropyl methylamine, debehenylpropyl propylamine, debehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines. in some embodiments, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenam idopropyldiethylamine, behenamidoethyldiethylamine, behenamidoethyldimethylamine, arachidamidopropyldimethylamine, arachidamido-propyidiethylamine, arachidam idoethyidiethylamine, arachidam idoethyidimethylamine, brassicam idopropyldimethylamine, lauram idopropyl dimethylamine, myristam idopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

Glyceryl Ester (Glycerol Esters)

The at least one glyceryl ester may be chosen from glycerol ester of fatty acids or glyceryl esters (or glycerol fatty esters), for example, glyceryl monomyristate, glyceryl monopalmitate, glyceryl monostearate, glyceryl isostearate, glyceryl monooleate, glyceryl dioleate, glyceryl distearate, glyceryl laurate, trilaurin, triarachidin, tribehenin, tricaprin, tricaprylin, caprylic/capric triglyceride, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

The at least one glyceryl ester may be selected from:

esters of an oligomeric glycerol, especially the esters of diglycerol, in particular the condensates of adipic acid and of glycerol, for which a portion of the hydroxyl groups of the glycerols have reacted with a mixture of fatty acids, such as steric acid, capric acid, stearic and isostearic acid and 12-hydroxystearic acid, such as, in particular, those sold under the trade mark SOFTISAN 649 by the company Cremer Oleo or under the trademark SP SUPERMOL B MBAL-SS-(RB) by the company Croda, such as bis-diglyceryl polyacyladipate-2, the arachidyl propionate sold under the trade mark WAX-ENOL 801 by Alzo, phytosterol esters, triglycerides of fatty acids and derivatives thereof, such as hydrogenated cocoglycerides, noncrosslinked polyesters resulting from the poly condensation between a linear or branched C4-C50 dicarboxylic acid or polycarboxylic acid and a C2-C50 diol or polyol, aliphatic esters of an ester resulting from the esterification of an aliphatic hydroxycarboxylic acid ester with an aliphatic carboxylic acid, or mixtures thereof.

In certain embodiments, the at least one glyceryl ester is selected from bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, or a mixture thereof.

In an embodiment, the at least one glyceryl ester is bis-diglyceryl polyacyladipate-2.

In an embodiment, the at least one glyceryl ester comprises bis-diglyceryl polyacyladipate-2 and optionally, a second glyceryl ester.

The total amount of the glyceryl ester(s) in the composition, if present, may vary but is typically from about 0.1 to about 10 wt. %, based on the total weight of the composition. In some instances, the total amount of glyceryl ester(s) is from about 0.1 to about 8 wt. %, about 0.2 to about 8 wt. %, about 0.2 to about 7 wt. %, about 0.2 to about 6 wt. %, about 0.5 to about 5 wt. %, about 1 to about 5 wt. %, about 1.5 to about 4 wt. %, about 1.75 to about 3.5 wt. %, or about 2 to about 3 wt. %, based on the total weight of the composition, including ranges and sub-ranges there between.

Thus, any one of the at least one glyceryl ester is present, by weight, based on the total weight of the composition, from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, to about 10 wt. %, including increments and ranges therein and there between.

Fatty Alcohol

In accordance with the disclosure, compositions hereof include at least one fatty alcohol.

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the hair treatment compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In particular, it is possible to mention, alone or as a mixture: lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol).

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C=C double bond), and contain from 12 to 40 carbon atoms.

The liquid fatty alcohols may be represented by: R-OH, wherein R denotes a C12-C24 branched alkyl group or an alkenyl group (comprising at least one C12-C24 double bond C=C), R being optionally substituted by one or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair treatment compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair treatment compositions preferably include cetearyl alcohol.

In accordance with the various embodiments, when present, the amount of each of the at least one fatty alcohol is from about 0.1° A to about 10%, or from about 0.1° A to about 8%, or from about 0.2% to about 7%, or from about 1° A to about 5%, or from about 1.2% to about 4.5% or any suitable combination, sub-combination, range, or sub-range thereof by weight, based on the weight of the composition. One of ordinary skill in the art, however, will appreciate that other ranges are within the scope of the invention. In some particular embodiments, at least one fatty alcohol is present from about 0.5 wt. % to about 15%, and in some particular embodiments present from about 1% to about 5 wt. %.

Thus, any one of the at least one fatty alcohol is present, by weight, based on the total weight of the composition, from about 0.1, 0.2, 0.3, 0.4, 0.5, 0.6, 0.7, 0.8, 0.9, 1, 1.1, 1.2, 1.4, 1.5, 1.6, 1.8, 2, 2.5, 3, 3.5, 4, 4.5, 5, 6, 7, 8, 9, to about 10 wt. %, including increments and ranges therein and there between.

Polyols

The term "polyol" should be understood as meaning, within the meaning of the present disclosure, an organic molecule comprising at least two free hydroxyl groups. The polyols of the cosmetic composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the compositions of the present disclosure, in certain instances, include ethylene glycol, propylene glycol, butylene glycol, hexylene glycol, glycerin, diglycerin, diethylene glycol, and dipropylene glycol, and mixtures thereof. In some cases, the polyol is butylene glycol. In some further cases, the polyol is one or both of propylene glycol and butylene glycol. Additionally, in some cases, the compositions comprise at least butylene glycol, and optionally one or more polyols other than butylene glycol.

Non-limiting examples of polyols that may, optionally, be included in the cosmetic include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, diethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

In one or more embodiments, the at least one polyol comprises one or more glycol compounds. In further embodiments, the glycol compounds are selected from the group consisting of hexylene glycol, butylene glycol, propylene glycol, dipropylene glycol, and combinations thereof. In other embodiments, the at least one polyol comprises glycerin.

In other embodiments, the at least one polyol comprises glycerin and at least one glycol selected from the group consisting of hexylene glycol, butylene glycol, propylene glycol, dipropylene glycol, and combinations thereof.

In some embodiments, the total amount of the at least one polyol may be at least 0.1 wt. % to about 10 wt. %, at least 0.5 wt. % to about 8 wt. %, at least 1 wt. % to about 7 wt. %, at least 1.5 wt. % to about 6 wt. %, based on the total weight of the hair treatment composition, including ranges and sub-ranges there between.

Water

The amount of water in the hair treatment compositions may be at least 50 wt. %, or from about 50 to about 95 wt. %, about 50 to about 90 wt. %, about 60 to about 88 wt. %, about 70 to about 87 wt. %, based on the weight of the composition.

Oils

Silicone Oil

The at least one silicone oil that may be present in the compositions of the present disclosure may be selected from polyalkylsiloxanes, polyarylsiloxanes, polyalkarylsiloxanes, polyestersiloxanes, polyphenylsilicones, and a mixture thereof.

The term "silicone oil" is interchangeable with the terms "polysiloxane" and "polysiloxane oil." For purposes of the instant disclosure, "amino silicones" are not considered a "silicone oil." Instead, amino silicones form an independent category of component that may optionally be included in the hair treatment compositions.

Non-limiting examples of silicone oils include polyalkylsiloxanes, polyarylsiloxanes, polyalkarylsiloxanes, polyestersiloxanes, polyphenylsiloxanes and a mixture thereof. In some instances, the silicone oil is preferably water insoluble at room temperature.

Representative examples of non-volatile, non-phenyl silicone oils which may be mentioned include cyclopentasiloxane, polydimethylsiloxanes; alkyl dimethicones; vinylmethyl methicones; and also silicones modified with aliphatic groups. It should be noted that "dimethicone" (INCI name)

corresponds to a poly(dimethylsiloxane) (chemical name), which is particularly preferred in some instances.

The silicone oils are preferably chosen from non-volatile dimethicone oils. In particular, these oils can be chosen from the following non-volatile oils:
- polydimethylsiloxanes (PDMSs),
- PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference Abil Wax 9801 from Evonik Goldschmidt,
- PDMSs comprising aliphatic groups, or functional groups such as hydroxyl, thiol and/or amine groups,
- polyalkylmethylsiloxanes substituted with functional groups such as hydroxyl and thiol groups,
- polysiloxanes modified with fatty acids, fatty alcohols or polyoxyalkylenes, and mixtures thereof.

Preferably, non-volatile and non-phenyl silicone oils are chosen from polydimethylsiloxanes; alkyl dimethicones and also PDMSs comprising aliphatic groups, in particular $C_2$-$C_{24}$ alkyl groups.

The silicone oil may be chosen from silicones of the following formula:

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms, a vinyl radical, or a hydroxyl radical,
X is an alkyl radical containing from 1 to 6 carbon atoms, or a hydroxyl radical,
n and p are integers chosen so as to have a fluid compound, in particular of which the viscosity at 25° C. is between 1 centistokes (cSt) and 1,000,000(cSt).

As non-volatile non-phenyl silicone oils which can be used according to the invention, mention may be made of those for which:
- the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
- the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker,
- the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning,
- the substituents $R_1$ to R6 represent a methyl group, the group X represents a hydroxyl group, and n and p are such that the viscosity is 700 cSt, for example the product sold under the name Baysilone Fluid TO.7 by the company Mom entive.

In some embodiments, it is preferable that the hair treatment compositions include two or more silicone oils, for example, two or more silicone oils selected from polyalkylsiloxanes, polyarylsiloxanes, polyalkarylsiloxanes, polyestersiloxanes, and a mixture thereof. In some instances, the two or more silicone oils are preferably two or more silicone oils selected from polyalkylsiloxanes (e.g., dimethicones) and cyclopentasiloxane. It is especially useful to include two or more silicone oils wherein at least one silicone oil has a viscosity of about 1 to 1000 centistokes and at least one silicone oil has a viscosity greater than 1000 to about 1,000,000 centistokes at 25° C. Centistokes is a standard unit used in the silicone industry for characterizing silicone oils because it is a representation of cinematic viscosity, which provides a better description of the behavior of silicone oils, as opposed to a dynamic viscosity (often represented by mPa.s). The viscosity of the silicone oils can be determined by methods known in the art, for example, using the Stokes viscosity or even a rotational viscometer.

The silicone oils having a viscosity of about 5 to 1000 cSt, may also have a viscosity of about 50 to about 1000 cSt, about 100 to about 1000 cSt, about 50 to about 750 cSt, about 100 to about 750 cSt, about 50 to about 500 cSt, about 100 to about 500 cSt, about 150 to about 500 cSt, about 200 to about 500 cSt, or about 350 cSt, including all ranges and subranges there between.

Non-Silicone Oils

The at least one non-silicone oil includes, for example, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Fluoro Oils

The one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The one or more hydrocarbon-based oils may be a saturated hydrocarbon, an unsaturated hydrocarbon, lipids, triglycerides, a natural oil or plant-based oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) ethers containing from 10 to 40 carbon atoms;

(iii) linear or branched hydrocarbons of mineral or synthetic origin, such as petroleum jelly, polydecenes, hydrogenated polyisobutene such as Parleam, and 4 0 squalane;

(iv) esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is 10, for instance Purcellin oil (cetearyl octanoate), isopropyl myristate, isopropyl palm itate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates; or cetyl esters;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched C $C_8$-$C_{16}$ esters, and isohexyl neopentanoate.

The total amount of all oil(s) (except for the optional aminosilicone, which is not considered a silicone oil according to the instant disclosure) in the hair treatment compositions can vary but is typically about 0.1 to about 50 wt. %, based on the total weight of the hair treatment composition. In some instances, the total amount of oil(s) may be about 0.1 to about 40 wt. %, about 0.1 to about 30 wt. %, about 0.1 to about 20 wt. %, about 0.1 to about 18 wt. %, about 0.1 to about 15 wt. %, about 0.1 to about 12 wt. %, about 0.1 to about 10 wt. %, about 0.1 to about 8 wt. %, about 0.5 to about 6 wt. %, or about 0.5 to about 5 wt. %, based on the total weight of the hair treatment composition, including all ranges and subranges there between.

Organic Solvents

The hair-treatment compositions may optionally include at least one organic solvent (non-silicone solvents).

Non-limiting examples of organic solvents include, for example, alcohols (for example, $C_{1-15}$, $C_{1-10}$, or $C_{1-6}$ alcohols), organic solvents, polyols (polyhydric alcohols and glycols (e.g., glycerin, butylene glycol, caprylyl glycol, etc.), and a mixture thereof.

Non-limiting examples of organic solvents include monoalcohols and polyols such as ethyl alcohol, isopropyl alcohol, propyl alcohol, benzyl alcohol, and phenylethyl alcohol, or glycerin or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of organic solvents include alkanediols such as 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol;

alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount organic solvent(s) in the hair treatment composition, if present, can vary but is typically about 0.1 to about 10 wt. %, based on the total weight of the hair treatment composition. In some cases, the total amount of water-soluble solvent(s) is about 0.1 to about 8 wt. %, about 0.1 to about 6 wt. %, about 0.1 to about 0.5 to about 10 wt. %, about 0.5 to about 8 wt. %, about 0.5 to about 6 wt. %, about 0.5 to about 5 wt. %, about 1 wt. %, about 2 wt. %, about 3 wt. %, or about 4 wt. %, including all ranges and subranges there between.

Other Components

In one or more embodiments, the hair treatment compositions described herein may contain one or more additional ingredients. Examples include, but are not limited to surfactants, emulsifiers, thickeners (such as polysaccharide-based or acrylate-based thickeners), aminosilicones, film formers, other polymers, fragrance, pH adjusters, and preservatives. Additional details regarding such additional ingredients follows below.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

In an embodiment, the compositions of the present disclosure are in the form of a leave-on cream product such as a styling/shaping product, leave-on product for curly hair (such as combing creams), anti-frizz hair product, or rinse-off or leave-on mask product.

In an embodiment, the compositions of the present disclosure are in the form of a rinse-off cream product such as a mask product.

In an embodiment, the compositions of the present disclosure are in the form of a leave-on cream product such as a styling/shaping product.

In an embodiment, the compositions of the present disclosure are in the form of a leave-on cream product such as a styling/shaping and conditioning product.

In an embodiment, the compositions of the present disclosure are in the form of a leave-on or a rinse-off styling conditioner.

In an embodiment, the compositions of the present disclosure are in the form of an emulsion such as an oil-in-water emulsion or a water-in-oil emulsion.

Methods

Another aspect of the invention pertains to methods of using the hair treatment compositions described herein. The methods generally comprise applying any of the hair treatment compositions described to hair. The hair treatment compositions may be useful in a variety of settings, and either for chemically treated or untreated hair. Use on treated hair can include chemically relaxed/straightened hair or chemically dyed or bleached or lightened/highlighted hair. Use on hair may include as part of a shampoo, part of a conditioner or as a conditioner, as a pre-treatment, or after cleansing or conditioning or washing the hair as a leave-on treatment for styling/shaping the hair or caring for curly hair or as a leave-on or rinse-off mask treatment.

Methods of treating hair according to the disclosure may include applying a hair treatment composition of the instant disclosure to the hair (wet, damp, or dry hair), allowing the hair treatment to remain on the hair for a sufficient amount of time, and rinsing the hair treatment composition from the hair or allowing the hair treatment to be left on the hair as a leave-on product. The hair treatment composition may be applied to the hair before, during, or after other hair treatment compositions (e.g., a shampoo, a conditioner, a mask, a cream, a lotion, a gel, etc.).

Other methods of treating hair according to the disclosure involve a wash and go/braiding technique. Typically, the hair type on which this method is used is curly hair.

Other methods of treating hair according to the disclosure involve a twist out technique. Typically, the hair type on which this method is used is curly hair.

The hair treatment composition may be allowed to remain on the hair for a period of time, for example from about a few seconds (1, 3, 5, or 10 seconds) to about 10, 20, or 30 minutes, or longer.

The hair treatment compositions of the present disclosure can be used on hair of various curl types, the curl types ranging from slightly wavy to very kinky and coily hair.

The hair treatment compositions may be useful for treating chemically treated hair.

Described above is the individual application of a hair treatment composition or the combined or layered application of a hair treatment composition with another composition. In some cases, a hair treatment composition is individually applied to the hair and also combined or layered with another composition that is also applied to the hair.

Kits

The hair treatment compositions of the instant disclosure may be incorporated into a kit. For example, the kits may include at least one hair treatment composition according to the instant disclosure. The kits may also include one or more hair treatment compositions (according the instant disclosure), a shampoo and/or a conditioner and/or a mask.

Implementation of the present disclosure is provided by way of the following examples. The examples serve to illustrate the technology without being limiting in nature.

EXAMPLES

The following Examples are intended to be non-restrictive and explanatory only.

The ingredient amounts in the compositions/formulas described below are expressed in % by weight, based on the total weight of the composition.

Several formulas were produced having the ingredients as listed in the tables below. The balance of all formulas was water.

Example I

Compositions

TABLE 1

| TYPE | US INCI NAME OF INGREDIENTS | FORMULAS Wt. % (Active) | | | |
|---|---|---|---|---|---|
| | | A | B | C | D |
| CATIONIC CELLULOSIC QUATERNARY AMMONIUM COMPOUND | POLYQUATERNIUM-4 | 0.25 | 0.25 | 0.25 | 0.25 |
| NONIONIC POLYSACCHARIDE | PECTIN | 0.2 | 0.2 | 0.2 | 0.2 |
| CATIONIC SURFACTANT | BEHENTRIMONIUM CHLORIDE | 2.4 | 2.4 | 2.4 | 2.4 |
| GLYCERYL ESTER | BIS-DIGLYCERYL POLYACYLADIPATE-2 | 2 | 2 | 2 | 2 |
| FATTY ALCOHOL | CETEARYL ALCOHOL | 4.5 | 1.2 | 1.2 | 4.5 |
| POLYOL | BUTYLENE GLYCOL AND/OR GLYCERIN | 4 | 5 | 5 | 4 |
| OTHER ESTERS | CETYL ESTERS | 0.6 | 0.3 | 0.3 | 0.6 |
| | GLYCERYL STEARATE SE | 1-2 | 1-2 | 1-2 | 1-2 |
| | HYDROXYPROPYL GUAR OR HYDROXYETHYLCELLULOSE | 0-1 | 0-1 | 0-1 | 0-1 |
| POLYSACCHARIDE-BASED THICKENERS | HYDROXYPROPYL GUAR HYDROXYPROPYLTRIMONIUM CHLORIDE | 0-1 | 0-1 | 0-1 | 0-1 |
| OILS (SILICONE AND/OR NON-SILICONE OILS) | NATURAL OR PLANT-BASED OILS | 0-5 | 0-5 | 0-5 | 0-5 |
| MISCELLANEOUS OR ADDITIVES | VITAMINS, PRESERVATIVES, PLANT EXTRACTS, SUGAR, SHORT CHAIN ALCOHOLS, FRAGRANCE | 0-5 | 0-5 | 0-5 | 0-5 |
| SOLVENT | WATER | QS 100 | QS 100 | QS 100 | QS 100 |

Process of making the invention composition:

This formula was prepared by mixing part of the water, the cationic cellulosic quaternary ammonium compound and pectin. Next, the batch was heated to 65 degrees C. and the oil phase containing the fatty alcohols, oils, and glyceryl ester was added. After the emulsion was created, the cooling process was started by adding the remainder of water, polyols, and desired additives such as preservatives, and fragrance.

Example II

Testing the Contribution of Various Ingredients

Protocol for Treating Hair Swatches:

Non-chemically treated hair swatches (curly hair type) were prepared for the test and labelled (three swatches per test formula). The swatches were treated as follows:
1. Swatches were treated with cleansing shampoo: 30 seconds washing with water, 30 seconds shampoo application and 30 seconds rinsing with water.
2. The wet swatches were combed from root to end.
3. 2.5 gm of test product was applied on each swatch from root to end.
4. Each swatch was scrunched from bottom to top and placed on aluminum foil.

5. The swatches were allowed to air dry overnight
6. Steps 1 to 5 were repeated for each sample/swatch.
7. After 12 hours (in the morning), the swatches were evaluated by at least 5 evaluators and a salon expert. The results are presented in Table 2 below.

Commercial Product E ingredients:
  Water, Shea Butter, Coconut Oil, Macadamia Ternifolia Seed Oil, Mango Seed Butter, Avocado Oil, Glycerin, Aloe Barbadensis Leaf Extract, Neem Seed Oil, Carrot Seed Oil, Sorbitol Esters, Vitamins, Plant Extracts, Proteins.

TABLE 2

| Ingredient | Formula Texture Thickening | Conditioning | Hold/ Control | Curl Definition | Frizz Control | Curl Pickup | Discipline |
|---|---|---|---|---|---|---|---|
| Polyquaternium-4 (Comparative formula X - modified formula A without pectin) | Softer thick cream | ✓ | | | | ✓ | |
| Pectin (Comparative formula Y - modified Formula A without polyquaternium-4) | Thicker than invention Formula A and comparative formula X | | | | | | ✓ |
| Polyquaternium-4 + Pectin INVENTION (Formula A) | Softer thick cream | ✓ | ✓ | ✓ | ✓ | ✓ | ✓ |

✓: Performance achieved on hair swatches

Table 2 (see above) explains the contribution of polyquaternium-4 and pectin when incorporated separately and when the two are used in combination. The formulas were use on hair swatches as leave-on treatments.

The formula with Polquaternium-4 alone (Comparative Formula X) provided good conditioning benefits and curl pickup and the formula with pectin alone (Comparative Formula Y) provided discipline to the hair and had a consistency that was thicker than those of Comparative Formula X and the inventive formula. However, surprisingly and unexpectedly, a unique synergy was observed when the ingredients were added in combination, resulting in a formula that provided exceptional and additional properties of hold/control, curl definition, frizz control, curl pickup and discipline. The formulas with only one of the two ingredients did not provide all these attributes.

At the same time, the inventive formula had a desirable consistency of a thick cream that was softer than that of Comparative Formula Y. The consistency of the inventive formula was more desirable because it provided good application and spreadability properties on hair.

Example III

Performance Tests on Hair on the Heads of Human Volunteers and Comparisons to Oil-Based Compositions The invention was tested with several techniques such as the wash and go method and the twist out method. The wash and go method is when the product is applied to wet or damp hair and left to air dry or diffuse. Braiding and applying is the usual wash and go technique on curly hair types for leave on products. The twist out method is when the product is applied to freshly washed hair and the hair is twisted to obtain styles such as ringlets, large curls and chaotic waves.

The performance of the invention composition in Table 1 on hair was compared to the performance of two commercial products that were claimed for use on curly hair in a wash and go test.

Commercial Product F ingredients:
  Water, Castor Seed Oil, Cetearyl Alcohol, Cetearyl Olivate, Glycerin, Sorbitan Olivate, Shea Butter, Rice Extract, Rice Amino Acids, Hydrolyzed Quinoa, Keratin Amino Acids, Avocado Oil, Linseed Seed Oil, Salvia Hispanica Seed Oil, Plant Ferment Extract and Filtrate, Cellulose Gum, Xanthan Gum, Microcrystalline Cellulose.

Before the wash and go tests, the hair (curly hair type) of a human volunteer was first cleansed with a shampoo and then treated with a rinse off conditioner. The hair was kept wet and was divided into two sides.

Example IIIA

The invention formula A in Table 1 was applied on the hair on the left side of the head in a section by section manner from roots to ends on one side and braided while commercial product E was applied on the other right side and braided in the same manner. The composition/product were used as leave-on treatments on the hair (i.e., they were not rinsed off from the hair). The hair was air-dried and then deconstructed, meaning the braids were taken out. The hair was assessed by hair salon experts (see FIG. 1).

Figure 1:
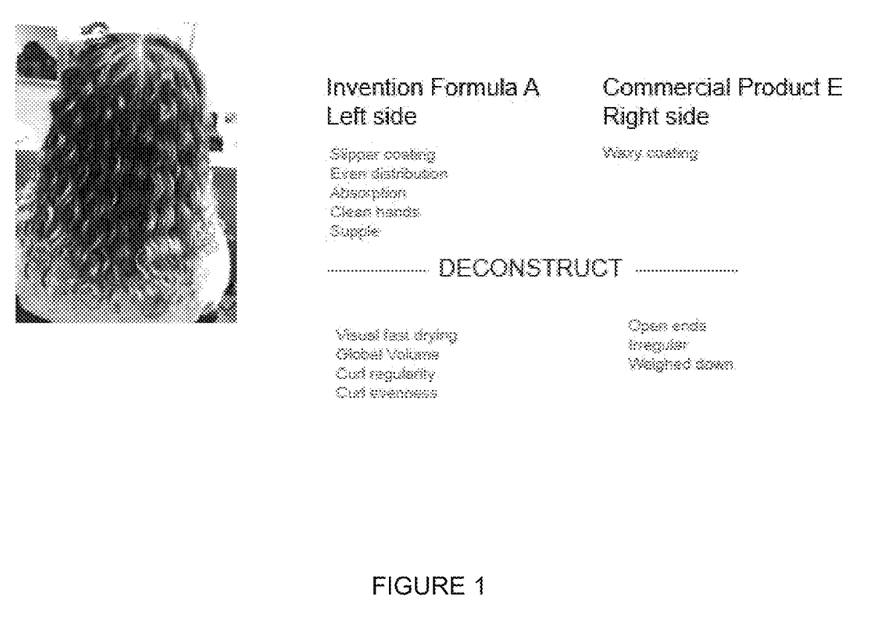
FIGS. 1 includes pictures of hair of a human volunteer in which the left side was treated with the composition of the invention and the right side was treated with a comparative commercial product. The hair was treated according to a wash and go/braiding technique.

Before the braids were deconstructed, some of the salon experts commented that the hair on the left side which was treated with the invention had slippery coating, distributed evenly, and absorbed on hair. It left the hands clean (not sticky), and the hair supple. On the other hand, the hair on the right side exhibited a waxy coating.

After deconstruction, the hair on the left side which was treated with the invention appeared to dry fast and had global volume. The hair exhibited curl regularity and evenness whereas the hair on the right side which was treated with the commercial product had open ends and irregular curls and was weighed down.

Example IIIB

The invention formula A in Table 1 was applied on the hair on the left side of the head in a section by section manner from roots to ends on one side and braided while commercial product F was applied on the other right side and braided in the same manner. The composition/product were used as leave-on treatments on the hair (i.e., they were not rinsed off from the hair). The hair was air-dried and then deconstructed, meaning the braids were taken out. The hair was assessed by hair salon experts (see FIG. 2).

Figure 2:
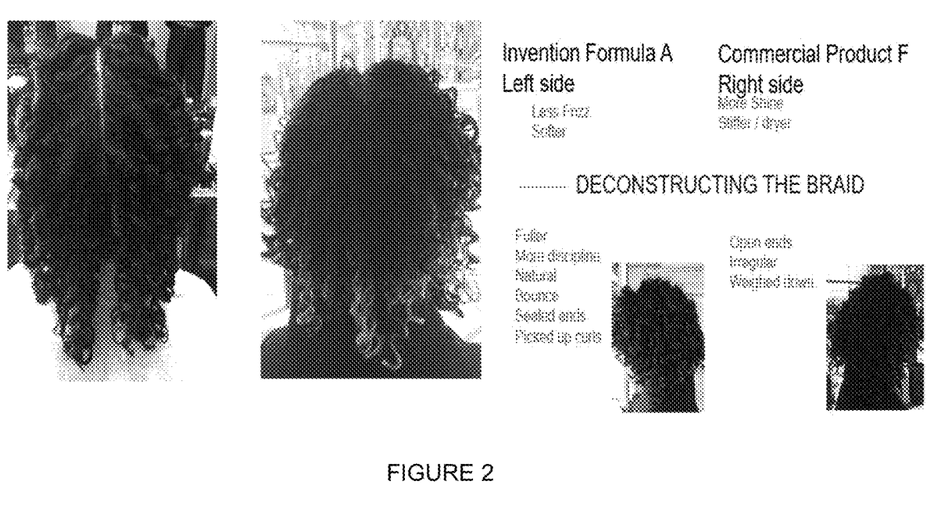
FIGS. 2 includes pictures of hair of a human volunteer in which the left side was treated with the composition of the invention and the right side was treated with a second comparative commercial product. The hair was treated according to a wash and go/braiding technique.

Before the braids were deconstructed, some of the salon experts commented that the hair on the left side which was treated with the invention had less frizz and was softer whereas the hair on the right side which was treated with the commercial product was stiffer and dryer.

After deconstruction, the hair on the left side which was treated with the invention resulted in the hair looking fuller and disciplined. It looked and felt more natural, had bounce, sealed ends and picked up curls whereas the hair on the right side which was treated with the commercial product had open ends and irregular curls and was weighed down.

It was also observed that the commercial product E which is formulated mainly with oils produced a heavy coating on the hair. The commercial product F created a stiffness to the hair and weighed it down. In contrast, the invention composition left the hair looking and feeling more natural while having bounce and movement. It exhibited more discipline, had excellent hold and control, picked up curls, and sealed the ends of the hair fibers as well as curl regularity, curl evenness, and volume.

Example IV Consumer Assessments

A consumer test involving women with curly hair was conducted in which the inventive formula was used by the women and compared to their usual routine of caring/styling the hair. The consumers found that the formula was multi-beneficial, i.e., it provided both caring and styling benefits. The attributes/benefits found were:

helped detangle the hair
curl definition
soft and silky
clean
glossy
hydrated
long lasting Most of the consumers commented that they would replace or add this product to their routine.

Example V Stylist Assessments

Hair stylists assessed the performance of the inventive formula on women with curly hair. The attributes/benefits found were:

thick like a curl pudding.
good for thick hair,
defined curl.
hydrating,
absorbs quickly
no film/residue to the hair
moisture/softness
shine
hold
last on hair for at least 3 days
Good for twist styles The results in examples IV and V above show that the invention formula provided both caring and styling/shaping benefits that typically would be provided by different types of formulations.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

The term "substantially free" or "essentially free" as used herein may also mean that the specific material is not added to the composition but may still be present in a raw material that is included in the composition.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair treatment composition comprising:
    (a) about 0.1 to about 4 wt. %, based on the total weight of the hair treatment composition, of polyquaternium-4;
    (b) about 0.1 to about 4 wt. %, based on the total weight of the hair treatment composition, of pectin;
    (c) 1.5 to about 5 wt.%, based on the total weight of the hair treatment composition, of behentrimonium chloride;
    (d) about 1 to about 10 wt. %, based on the total weight of the hair treatment composition, of bis-diglyceryl polyacyladipate-2;
    (e) about 2 to about 10 wt. %, based on the total weight of the hair treatment composition, of a fatty alcohol chosen from cetearyl alcohol, cetyl alcohol, and stearyl alcohol;
    (f) about 0.1 to about 10 wt. %, based on the total weight of the hair treatment composition, of a polyol chosen from butylene glycol, propylene glycol, glycerine, and a combination thereof; and
    (g) water;
       wherein the weight ratio of the polyquaternium-4 to pectin is from about 1 to about 3.

2. The hair treatment composition of claim 1 being free of silicones.

3. A method of treating hair, the method comprising applying the composition of claim 1 to the hair.

* * * * *